United States Patent [19]

Wilk

[11] Patent Number: 5,183,471
[45] Date of Patent: Feb. 2, 1993

[54] LAPAROSCOPIC CANNULA

[76] Inventor: Peter J. Wilk, 185 W. End Ave., New York, N.Y. 10023

[21] Appl. No.: 825,158

[22] Filed: Jan. 24, 1992

[51] Int. Cl.$^5$ .................................................. A61M 25/00
[52] U.S. Cl. ..................................... 604/284; 604/264
[58] Field of Search ...................... 128/4, 3, 5, 6, 7, 8, 128/9, 264; 604/280, 284, 160–170

[56] References Cited

U.S. PATENT DOCUMENTS

| | | | |
|---|---|---|---|
| 3,960,143 | 6/1976 | Terada | 128/4 |
| 4,653,476 | 3/1987 | Bonnet | 128/4 |
| 4,683,879 | 8/1987 | Williams | 128/4 |
| 4,700,694 | 10/1987 | Shishido | 128/4 |
| 5,025,778 | 6/1991 | Silverstein et al. | 128/4 |

Primary Examiner—John D. Yasko
Assistant Examiner—Manuel Mendez
Attorney, Agent, or Firm—R. Neil Sudol; Henry D. Coleman

[57] ABSTRACT

A cannula for use in laparoscopy comprises a tubular member having a first opening at a distal end and second opening at a proximal end for enabling the longitudinal insertion through the tubular member of a first laparoscopic instrument. The tubular member is further provided with two auxiliary ports disposed on opposite sides of the tubular member and at longitudinally staggered locations. The two auxiliary ports define an auxiliary insertion path for an extra laparoscopic instrument.

4 Claims, 1 Drawing Sheet

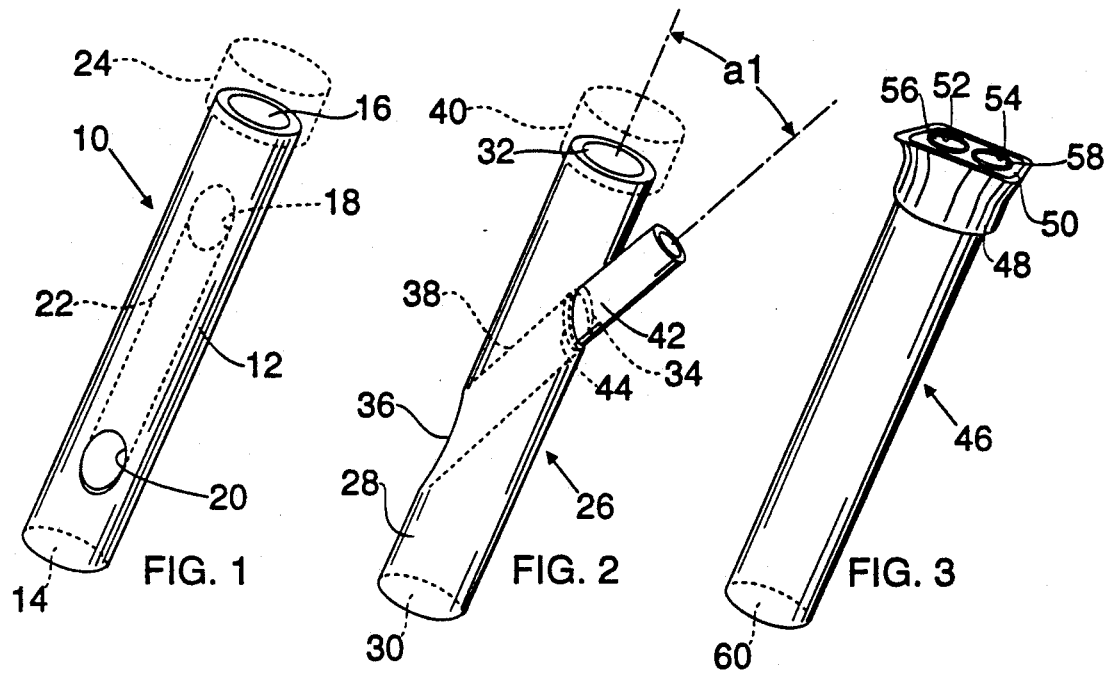
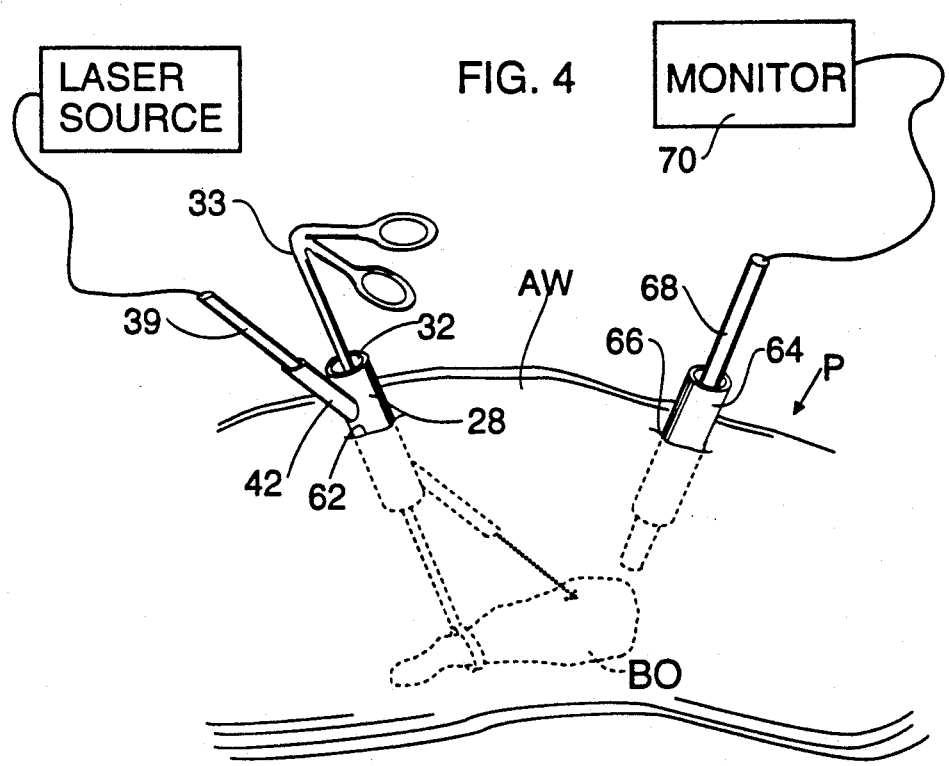

LAPAROSCOPIC CANNULA

BACKGROUND OF THE INVENTION

This invention relates to a cannula for use in laparoscopic surgery. This invention also relates to an associated surgical procedure.

Laparoscopy involves the piercing of a patient's abdominal wall and the insertion of a cannula through the perforation. Generally, the cannula is a trocar sleeve which surrounds a trocar during an abdomen piercing operation. Upon the formation of the abdominal perforation, the trocar is withdrawn while the sleeve remains traversing the abdominal wall. A laparoscopic instrument, such as a laparoscope or a forceps, is inserted through the cannula so that a distal end of the instrument projects into the abdominal cavity.

Generally, in a laparoscopic surgical procedure, three or four perforations are formed in the abdomen to enable deployment of a sufficient number of laparoscopic instruments to perform the particular surgery being undertaken. Each perforation is formed by a trocar which is surrounded by a sleeve, the sleeves or cannulas all remaining in the abdominal wall during the surgical procedure.

Prior to insertion of the first trocar and its sleeve, a hollow needle is inserted through the abdominal wall to enable pressurization of the abdominal cavity with carbon dioxide. This insufflation procedure distends the abdominal wall, thereby producing a safety space above the patient's abdomnal organs.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

It frequently occurs during laparoscopic surgery that an additional instrument is temporarily required. Inserting this extra instrument involves either temporarily removing one of the other instruments or forming another perforation with a trocar.

OBJECTS OF THE INVENTION

An object of the present invention a device and an associated method for facilitating laparoscopic surgery.

A particular object of the present invention is to provide is to provide a trocar sleeve or laparoscopic cannula which facilitates the temporary insertion of an extra laparoscopic instrument during a laparoscopic procedure.

A further particular object of the present invention is to provide a method for the temporary insertion of an extra laparoscopic instrument during laparoscopic surgery which does not require the formation of another perforation in the abdominal wall or the removal of another instrument from the abdomen.

An even more particular object of the present invention is to provide a trocar sleeve or laparoscopic cannula which is easy to use and to manufacture.

SUMMARY OF THE INVENTION

A cannula for use in laparoscopy comprises, in accordance with the present invention, a tubular member having a first opening at a distal end and second opening at a proximal end for enabling the longitudinal insertion through the tubular member of a first laparoscopic instrument. The tubular member is further provided with a first aperture or auxiliary port on a side of the tubular member distally of the second opening and a second aperture or auxiliary port on a substantially opposite side of the tubular member proximally of the first opening and distally of the second aperture. The first aperture and the second aperture define a linear path for a second laparoscopic instrument, the linear path being oriented at an acute angle with respect to the tubular member.

Pursuant to another feature of the present invention, a tubular arm is attached to the tubular member at the first aperture. That arm is oriented along the linear path defined by the first and second apertures, thereby facilitating insertion of the second laparoscopic instrument through the second aperture upon insertion of the second laparoscopic instrument through the first aperture.

The cannula may further comprise an insufflation stopper provided on the tubular member at the first aperture.

According to a more general conceptualization of the present invention, a cannula for use in laparoscopy comprises a tubular member, a first component on the tubular member for defining a first path through the tubular member for a first laparoscopic instrument, and a second component or components, disposed on the tubular member and at least partially separate from the first component, for defining a second path through the tubular member for a second laparoscopic instrument.

Preferably, the first path and the second path extend at an acute angle relative to one another. Where the first path extends longitudinally through the tubular member, the second path extends at an acute angle relative to the tubular member.

In a more specific description of the cannula, the tubular member has a sidewall, while the second component includes a first aperture disposed in the sidewall on one side of the tubular member and a second aperture disposed in the sidewall on a substantially opposite side of the tubular member. The second aperture is disposed proximally of a distal end of the tubular member and distally of the first aperture.

Pursuant to an alternative feature of the present invention, the first path and the second path are approximately parallel to one another. In that event, the tubular member is provided at a proximal end with a substantially transverse wall, and the first component and the second component include separate and respective openings in the transverse wall. Insufflation stoppers may be provided at the openings in the transverse wall for inhibiting release of gaseous pressure through the openings.

A laparoscopic method in accordance with the present invention comprises the steps of (a) forming a perforation in a patient's abdominal wall, (b) disposing a cannula in the perforation, (c) inserting a distal end of a first laparoscopic instrument through the cannula and into the patient's abdominal cavity, and (d) inserting a distal end of a second laparoscopic instrument through the cannula and into the patient's abdominal cavity while the first laparoscopic instrument is partially disposed in the cannula. Upon the insertion of the second laparoscopic instrument, it is manipulated from outside the patient to perform a surgical operation inside the patient. Subsequently, the second laparoscopic instrument is withdrawn from the patient's abdominal cavity and from the cannula.

Pursuant to one alternative feature of the present invention, the second laparoscopic instrument is inserted through the cannula at an acute angle with respect to the first laparoscopic instrument. In that case, the second laparoscopic instrument is inserted through a pair of side ports disposed on opposite sides of the cannula and at locations staggered longitudinally or axially relative to one another.

Alternatively, the second laparoscopic instrument is inserted through the cannula essentially parallel to the first laparoscopic instrument. In that case, the first laparoscopic instrument is inserted through a first port at a proximal end of the cannula and the second laparoscopic instrument is inserted through a separate second port also at the proximal end of the cannula.

A laparoscopic cannula and the associated laparoscopic method in accordance with the present invention facilitate laparoscopic surgery by enabling the temporary insertion of an extra instrument during a laparoscopic procedure. Pursuant to the method of the present invention, an extra laparoscopic instrument may be inserted into a patient's abdomen during laparoscopic surgery without requiring the formation of another perforation in the abdominal wall or the removal of a previously deployed instrument from the abdomen.

BRIEF DESCRIPTION OF THE DRAWING

FIG. 1 is a schematic perspective view, on a reduced scale, of a trocar sleeve or laparoscopic cannula, in accordance with the present invention.

FIG. 2 is a schematic perspective view, on a reduced scale, of another trocar sleeve or laparoscopic cannula, in accordance with the present invention.

FIG. 3 is a schematic perspective view, on a reduced scale, of yet another trocar sleeve or laparoscopic cannula, in accordance with the present invention.

FIG. 4 is a schematic perspective view, on a reduced scale, of a laparoscopic surgical method, in accordance with the present invention, using the trocar sleeve or laparoscopic cannula of FIG. 2.

DETAIKLED DESCRIPTION

As illustrated in FIG. 1, a trocar sleeve or laparoscopic cannula 10 comprises a tubular member 12 having an exit opening 14 at a distal end and an insertion opening 16 at a proximal end for enabling the longitudinal passage through tubular member 12 of a first laparoscopic instrument (see FIG. 4). Tubular member 12 is further provided in a sidewall, distally of insertion opening 16, with an insertion aperture or port 18 on one side of tubular member 12. On a substantially opposite side of tubular member 12 is disposed an exit aperture or port 20 proximally of exit opening 14 and distally of insertion aperture 18. Apertures 18 and 20 define a linear passage or path 22 for a second laparoscopic instrument (see FIG. 4), the path being oriented at an acute angle with respect to tubular member 12. Trocar sleeve or laparoscopic cannula 10 is provided at its proximal end with a schematically represented conventional cap 24 which carries a one way valve or insufflation stopper (not illustrated).

As depicted in FIG. 2, another trocar sleeve or laparoscopic cannula 26 includes a body member in the form of a tube 28 having an exit opening 30 at a distal end and an insertion opening 32 at a proximal end for enabling the longitudinal passage through tube 28 of a first laparoscopic instrument 33 (FIG. 4). Tube 28 is further provided in a sidewall, distally of insertion opening 32, with an insertion aperture or port 34 on one side of tubular 28 member. Tube 28 is also provided in its sidewall with an exit aperture or port 36 on a substantially opposite side of tube 28, exit aperture 36 being located proximally of exit opening 30 and distally of insertion aperture 34. Apertures 34 and 36 define a linear passage or path 38 for a second laparoscopic instrument 39 (FIG. 4), the path being oriented at an acute angle al with respect to tube 28. Cannula 26 is provided at its proximal end with a schematically represented conventional cap 40 which carries a one way valve or insufflation stopper (not illustrated).

As further depicted in FIG. 2, cannula 26 includes a tubular arm 42 attached to tube 28 at insertion aperture 34. Arm 42 serves to guide auxiliary laparoscopic instrument 39 along passage or path 38. Accordingly, arm 42 is oriented along path 38 to facilitate insertion of auxiliary laparoscopic instrument 39 through exit aperture 36 upon insertion of laparoscopic instrument 39 through insertion aperture 34.

Cannula 26 is provided with an insufflation stopper 44 which is connected to tubular member 28 at insertion aperture 34.

FIG. 3 shows another trocar sleeve or laparoscopic cannula 46 provided at a proximal end with a cap 48 (schematically represented). End cap 48 includes a transversely oriented plate or wall 50 in which a pair of insertion openings or ports 52 and 54 are disposed. Each insertion port 52 and 54 is covered from the inside of cap 48 with a respect insufflation stopper or valve member 56 and 58 for inhibiting release of gaseous pressure through ports 52 and 54.

At an end opposite cap 48, cannula 46 has an exit opening 60. During a laparoscopic procedure, a primary laparoscopic instrument (not shown) may be inserted through port 52 along a substantially longitudinal path to exit opening 60. Subsequently, a second laparoscopic instrument (not shown) may be temporarily inserted through port 54 and exit opening 60. The operation of the two laparoscopic instruments simultaneously will be facilitated if the instruments have different shaft lengths. In that way, interference between the two instruments at the proximal end of trocar sleeve or laparoscopic cannula 46 will be minimized if not eliminated.

With cannula 46, the paths of the two laparoscopic instruments are approximately parallel to one another.

In performing a laparoscopic method utilizing a cannula 10, 26 or 46, a surgeon forms a perforation 62 (see FIG. 4) in an abdominal wall AW of a patient P. Upon the formation of perforation 62, a cannula as described hereinabove, for example, cannula 26, is disposed in the perforation so that cannula 26 traverses abdominal wall AW. A distal end of laparoscopic instrument 33, e.g., a grasping forceps, is inserted through tube 28 and into the patient's abdominal cavity (not designated). Subsequently, a distal end of auxiliary laparoscopic instrument 39 is inserted through tubular member 28 and into the patient's abdominal cavity while the first laparoscopic instrument 33 is partially disposed in cannula.26. More specifically, auxiliary instrument 39 is inserted through guide arm 42, tubular member 28 and exit aperture 36. Upon the insertion of auxiliary laparoscopic instrument 39, it is manipulated from outside the patient to perform a surgical operation inside the patient's abdomen. Subsequently, auxiliary laparoscopic instrument 39 is withdrawn from the patient's abdominal cavity and from the cannula 26.

During the afore-described procedure, another trocar sleeve or laparoscopic cannula 64 remains disposed in a respective perforation 66 in abdominal wall AW, an additional laparoscopic instrument 68 extending through cannula 64 into the patient's abdominal cavity. This third laparoscopic instrument 68 may take the form of a laparoscope or a video camera holder operatively connected to a monitor 70, another forceps, or another laparoscopic surgical instrument.

The auxiliary laparoscopic instrument 39 is most likely to take the form of an instrument which is needed only during a small portion of the entire laparoscopic procedure. Such an instrument might be, for example, a laser (shown in the drawing) or other cauterization instrument, an irrigator, a suction tube, an extra retractor, a clamp, a stapling or suturing device, or a clip applicator. The auxiliary laparoscopic instrument 39 operates on an internal body organ BO of patient P.

Naturally, trocar sleeve or laparoscopic cannular 10, 26, or 46 functions with relatively small-diameter instruments, as illustrated by the small sizes of instruments 33 and 39 (FIG. 4) relative to trocar tube 28. Of course, the diameter of a trocar sleeve or cannular in accordance with the present invention msut be larger than the combined diameter of the two laparoscopic instruments inserted through the cannular in order to ensure passage of both laparoscopic isntruments along their respective paths.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A cannula for use in laparoscopy, comprising a tubular member having a first opening at a distal end and second opening at a proximal end for enabling the longitudinal insertion through said tubular member of a first laparoscopic instrument, a first aperture being disposed on a side of said tubular member distally of said second opening, a second aperture being disposed on a substantially opposite side of said tubular member proximally of said first opening and distally of said first aperture, said first aperture and said second aperture defining a linear path for a second laparoscopic instrument, said linear path being oriented at an acute angle with respect to said tubular member.

2. The cannula defined in claim 1, further comprising a tubular arm attached to said tubular member at said first aperture.

3. The cannula defined in claim 2 wherein said tubular arm is oriented along the linear path defined by said first aperture and said second aperture, thereby facilitating insertion of the second laparoscopic instrument through said second aperture upon insertion of said second laparoscopic instrument through said first aperture.

4. The cannula defined in claim 1, further comprising an insufflation stopper provided on said tubular member at said first aperture.

* * * * *